United States Patent
Tybinkowski et al.

(10) Patent No.: US 6,831,961 B1
(45) Date of Patent: Dec. 14, 2004

(54) COMBINED TOMOGRAPHY SCANNERS

(75) Inventors: Andrew P. Tybinkowski, Boxford, MA (US); Robert F. Riemer, Andover, MA (US); Robert M. Williams, Wilmington, MA (US)

(73) Assignee: Analogic Corporation, Peabody, MA (US)

( * ) Notice: Subject to any disclaimer, the term of this patent is extended or adjusted under 35 U.S.C. 154(b) by 67 days.

(21) Appl. No.: 10/161,434

(22) Filed: Jun. 3, 2002

Related U.S. Application Data

(60) Provisional application No. 60/295,225, filed on Jun. 1, 2001.

(51) Int. Cl.[7] .................................................. A61B 6/00
(52) U.S. Cl. ........................ 378/4; 378/17; 250/363.04; 250/363.05
(58) Field of Search ............................. 378/4, 17, 193, 378/205, 204; 250/363.03, 363.04, 363.08, 363.05; 600/407, 425, 427, 436

(56) References Cited

U.S. PATENT DOCUMENTS

| | | | | |
|---|---|---|---|---|
| 4,961,208 A | * | 10/1990 | Okada .......................... | 378/18 |
| 5,391,877 A | * | 2/1995 | Marks .................... | 250/363.04 |
| 5,525,905 A | | 6/1996 | Mohapatra et al. ......... | 324/318 |
| 5,638,817 A | * | 6/1997 | Morgan et al. ............. | 600/425 |
| 5,960,054 A | | 9/1999 | Freeman et al. ............... | 378/4 |
| 5,969,358 A | * | 10/1999 | DiFilippo et al. ...... | 250/363.03 |
| 6,128,365 A | | 10/2000 | Bechwati et al. ............. | 378/57 |
| 6,173,031 B1 | | 1/2001 | Hoffman et al. .............. | 378/19 |
| 6,188,743 B1 | | 2/2001 | Tybinkowski et al. ......... | 378/4 |
| 6,256,528 B1 | * | 7/2001 | Zonneveld et al. .......... | 600/425 |
| 6,303,935 B1 | | 10/2001 | Engdahl et al. ........ | 250/363.03 |
| 6,337,894 B1 | | 1/2002 | Tybinkowski et al. ......... | 378/4 |
| 6,490,476 B1 | * | 12/2002 | Townsend et al. .......... | 600/427 |
| 6,580,777 B1 | * | 6/2003 | Ueki et al. .................... | 378/17 |
| 2003/0095635 A1 | * | 5/2003 | Moritake et al. ........... | 378/198 |

OTHER PUBLICATIONS

Townsend, et al., The Smart Scanner: A Combined PET/CT Tomograph for Clinical Oncology, Townsend et al, 1999, 5 pages.

Massager, et al, Neurosurg Focus 8(2), Combined Magnetic Resonance Imaging–and Positron Emission Tomography–Guided Stereotactic Biopsy In Brainstem Mass Lesions: Diagnostic In a Series of 30 Patients, Feb. 2000, 6 pages.

* cited by examiner

*Primary Examiner*—Edward J. Glick
*Assistant Examiner*—Therese Barber
(74) *Attorney, Agent, or Firm*—McDermott Will & Emery LLP

(57) ABSTRACT

A multi-scanner frame in accordance with the principles of the present invention includes a base and a plurality of stands. Each stand supports a tomography gantry. The plurality of scanners supported by the gantries may represent a plurality of tomography modalities. A linear guide allows for the ready movement of at least one of the gantries relative to one or more remaining gantries.

20 Claims, 4 Drawing Sheets

COMBINED TOMOGRAPHY SCANNERS

RELATED APPLICATION

This application claims the benefit of the U.S. Provisional Application Ser. No. 60/295,225, filed Jun. 1, 2001, entitled COMBINED TOMOGRAPHY SCANNERS, invented by that Andrew P. Tybinkowski, Robert Riemer, and Robert Williams, which application is hereby incorporated by reference in its entirety.

FIELD OF THE DISCLOSURE

The present disclosure relates generally to tomography systems and, more specifically, to a frame for supporting a plurality of tomography devices.

BACKGROUND OF THE DISCLOSURE

Computed tomography (CT) scanners have been used for over twenty-five years, primarily as medical diagnostic aids. A CT scanner may create a two-dimensional cross-sectional image of a patient by rotating one or more X-ray sources and detectors about a patient in a fixed axial position, irradiating the patient with X-rays, detecting radiation scattered by the patient's body, and computing an image from the scattering data. By incrementing the axial position and combining the resulting series of two-dimensional cross-section images, a CT scanner may assemble a three-dimensional image of a patient.

Typically, many of the components of a CT scanner are supported by an annular gantry having inner and outer rings. The gantry's outer ring is secured to a stand and the inner ring is mounted for rotation within the outer ring. Many of the components of the CT scanner, including X-ray source(s) and detector(s), high voltage power supply, a data acquisition module, and balancing weights, may be mounted to the inner ring of the gantry for rotation therewith. During a scanning procedure, a patient table is positioned through the center of the gantry and the X-ray source and detector are rotated about the table along with the inner ring. The X-ray source supplies energetic particles that penetrate the patient and are scattered by the patient's body into appropriately positioned detectors. The CT scanner analyzes the scattering information to compute a corresponding cross-sectional anatomical image.

A more recently developed imaging procedure, positron emission tomography (PET), employs radiation detectors arranged in a ring. An annular gantry typically supports the ring of detectors. In order to image a patient the patient is injected with a radioactive isotope that emits positrons and is positioned within the annular gantry. The detectors, referred to as scintillators, sense the emitted positrons. From energy, location, and time information gathered by the scintillators, the PET scanner may produce 3-dimensional images that reflect a quantization of physiochemical processes in the patient's body.

A variety of imaging results, such as magnetic resonance imaging (MRI), X-ray, PET, and CT results may be combined, by superimposing images for example, to take advantage of particular benefits of each procedure. At the same time, the combined imagery provides a more comprehensive view of anatomical and related physiochemical processes within a given patient.

The mass and bulk of any such imaging devices render them unwieldy at best and cumbersome at worst. Providing access to their constituent components for maintenance and repair presents a major obstacle to the efficient operation of such machines. Furthermore, any combination of such imaging devices, for example, a combined CT/PET scanner, only exacerbates the access difficulties. A system and method for providing ready access to tomographic equipment would therefore be highly desirable.

SUMMARY OF THE DISCLOSURE

A frame in accordance with the principles of the present invention is configured to support a plurality of gantries such as those that may house tomographic equipment. The frame includes a movable support that permits at least one of the supported gantries to be moved relative to another of the supported gantries and to thereby provide ready access to tomography equipment housed by one or more of the gantries. Such access is particularly advantageous for the maintenance and repair of the tomography equipment.

In an illustrative embodiment, the frame includes a linear guide that supports at least one gantry. The plurality of gantries supported by the frame may be arranged along a longitudinal axis, so that a patient may be positioned for simultaneous scanning by the plurality of tomographic device supported by the gantries. The linear guide may include a linear race, ball bushing bearings, or a shaft rail assembly, for example. In such an embodiment at least one of the gantries may be translated along the linear guide in the direction of the longitudinal axis in order to thereby separate two or more gantries. The separation thus provided between the gantries may provide access to components housed by one or more of the separated gantries. In an embodiment in which one or more of the gantries tilts to provide access to tomographic equipment housed by the gantry, the separation provided by motion along the linear guide provides room for the tilting of one or more of the gantries.

Although the gantries may support a variety of tomographic equipment, an illustrative embodiment includes one CT scanner and one PET scanner gantry. In this embodiment, the frame includes a base, a first stand fixed to the base for supporting a first of the gantries, and a second stand movably mounted on the base for supporting a second of the gantries. The second stand and the second gantry can thus be moved away from the first stand and the first gantry to increase access to the gantries. The frame may include a retractable extension that can be pulled out of the base of the frame to allow the movable stand to be moved further from the fixed stand.

BRIEF DESCRIPTION OF THE DRAWINGS

The above and further features, aspects, and advantages of the invention will be apparent to those skilled in the art from the following detailed description, taken together with the accompanying drawings in which.

DETAILED DESCRIPTION

Figure 1:
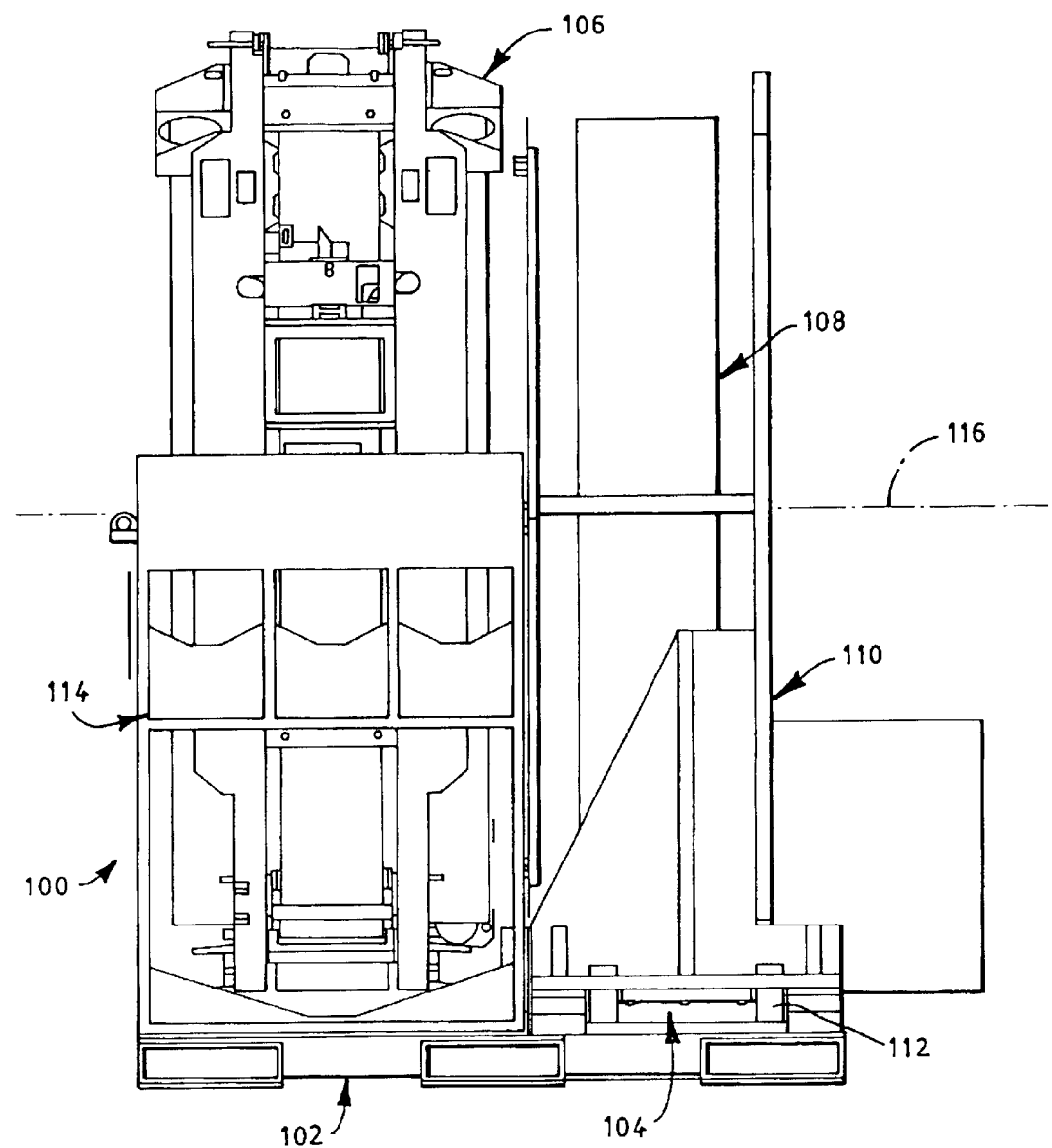
FIG. 1 is a side elevation view of a frame in accordance with the principles of the present invention.

A frame 100 in accordance with the principles of the present invention is illustrated in the side elevation view of FIG. 1. The frame 100 includes a base 102 and a linear guide 104. The linear guide 104 may include a linear race, ball bushing bearings, or a shaft rail assembly, for example. The linear guide 104 provides for translational support of one or more annular gantries. Such guides are available, for example, from Thomson Industries, Inc., Port Washington, N.Y., U.S.A. The frame 100 includes a plurality of gantries: an annular CT scanner gantry 106 and an annular PET scanner gantry 108 in this illustrative embodiment. The linear guide 104 operates as a movable support, allowing the PET scanner gantry 108 and associated movable stand 110 to be separated from the CT scanner gantry 106, by rolling upon ball bushing bearings for example, with very little effort. The linear guide may include a linear race, ball bushing bearings, or a shaft rail assembly, for example. One or more clamps 112, which may be frictional clamps, may be employed to hold the PET scanner gantry 108 and associated movable stand 110 in place after positioning. A frictional clamp such as may be employed may include a clamp piece with a radius machined into it to mate with a portion of the linear guide when activated.

In this illustrative embodiment, the CT scanner gantry is associated with a fixed stand 114 and the PET and CT scanners are aligned along a common axis 116. A patient may be placed on a table and inserted along the common axis 116 scanned by both scanners 106,108. The movable stand 110 and Pet scanner gantry 108 may be positioned, as shown, in close proximity to the CT scanner gantry 106 for normal operation, or may be separated from the CT scanner gantry in order to provide access to tomography components housed in or supported by either of the gantries 106,108.

Figure 2:
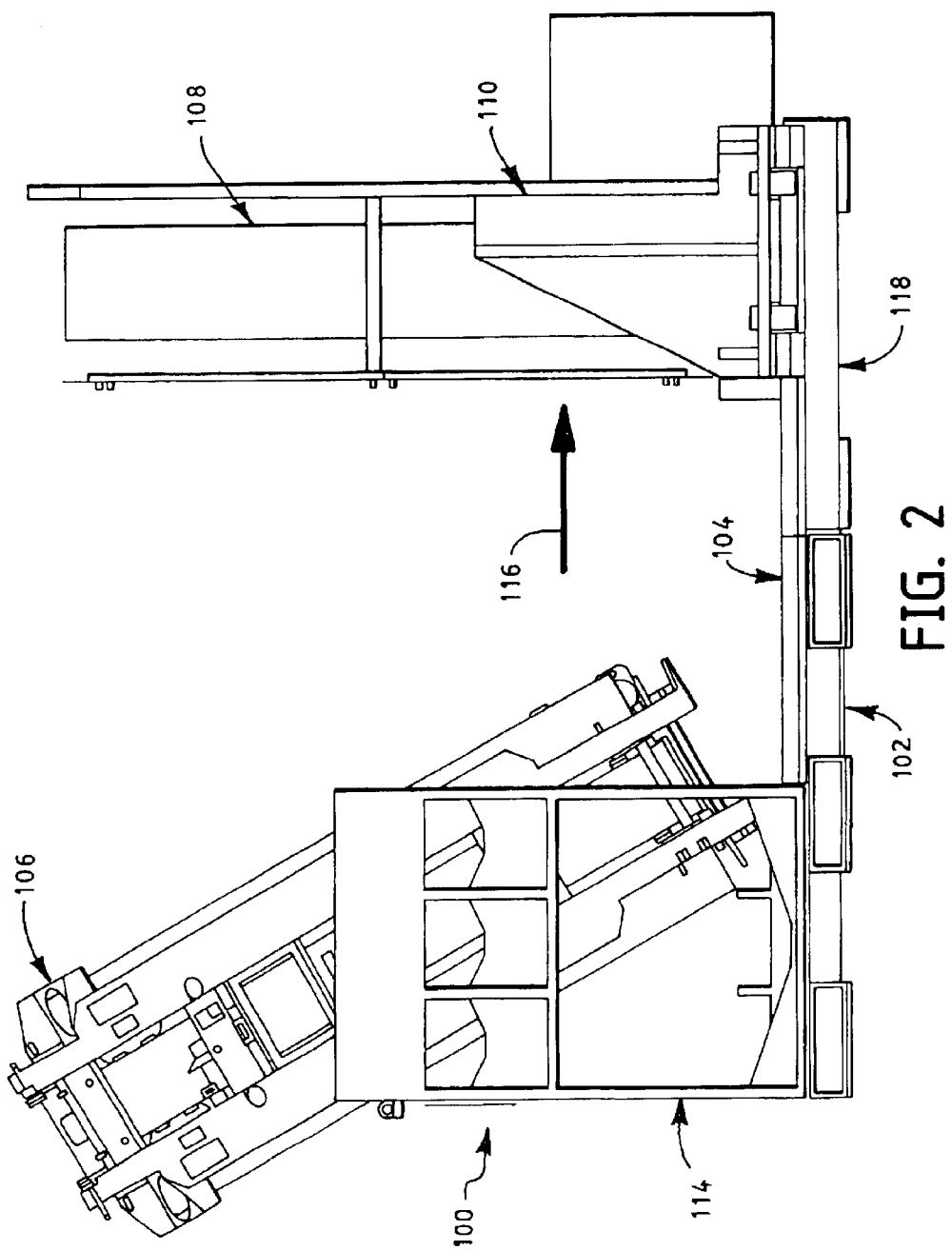
FIG. 2 is a side elevation view of a frame in accordance with the principles of the present invention in with gantries separated to provide access to tomography equipment supported by the gantries.

In the side elevation view of FIG. 2, the movable stand 110 and PET scanner gantry 108 have been moved in the direction indicated by the arrow 116 to separate the CT scanner gantry 106 and PET scanner gantry 108. By separating the gantries 106,108 in this fashion, access to the contents of either gantry is increased. Service personnel may use such access to carry out regular maintenance or to service equipment supported by the one or both of the gantries. Additionally, the additional space between the gantries 106, 108 provides sufficient room for a gantry, the CT gantry 106 in this illustrative embodiment, to be tilted. Such tilting provides even greater access to the components supported by the tilted gantry, gantry 106 in this illustrative embodiment. A gantry that includes means for pivotally mounting its outer support ring is discussed, for example, in U.S. Pat. No. 6,337,894 B1, issued Jan. 18, 2001 to Tybinkowski et al., which is hereby incorporated by reference in its entirety. In this illustrative embodiment, the base 102 includes a retractable extension 118, which can be pulled out to extend the track of the frame and allow the movable stand to be moved further from the fixed stand. The linear guide 104 may also be retractable, corresponding to the retractable base 118.

Figure 3:
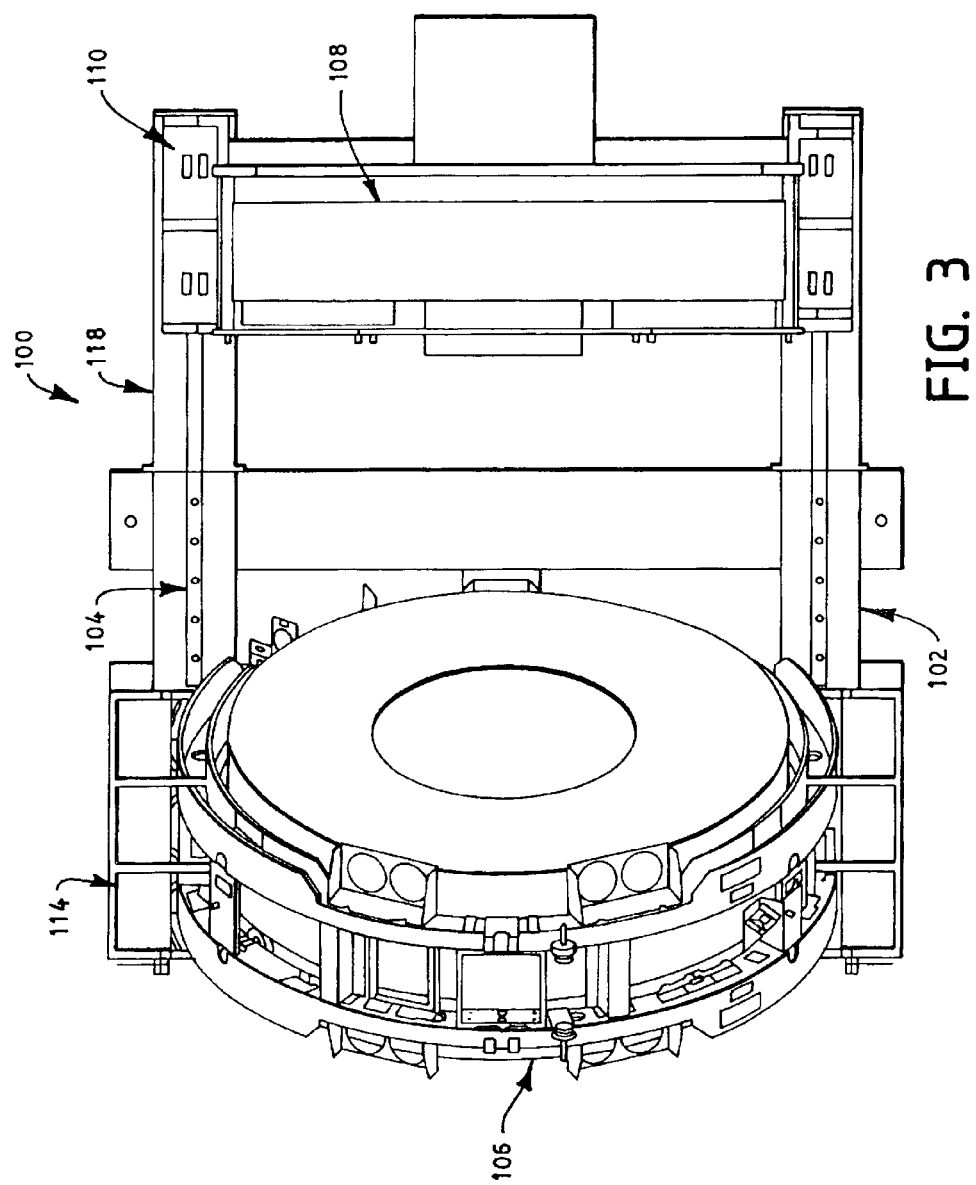
FIG. 3 is a top plan view of a frame in accordance with the principles of the present invention with two gantries separated and one gantry tilted to provide access to tomography equipment housed within the gantries.
Figure 4:
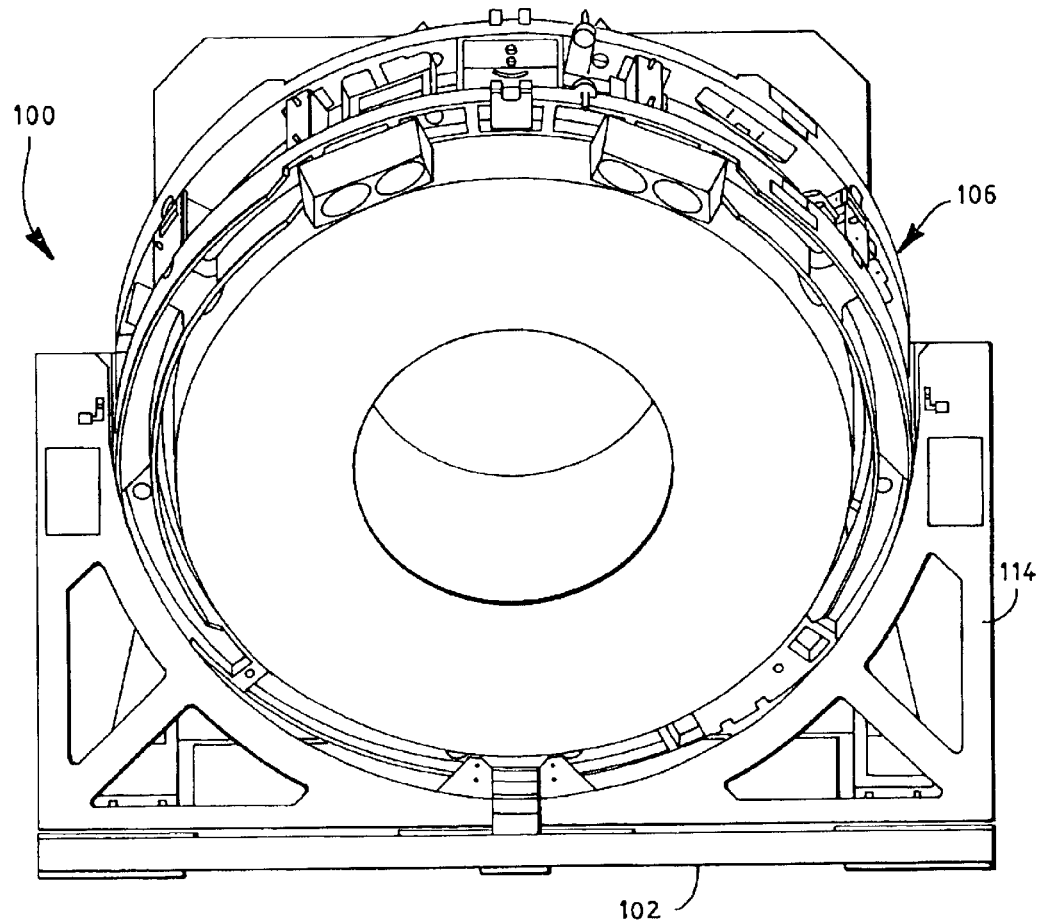
FIG. 4 is an end elevation view of a frame in accordance with the principles of the present invention in which one gantry is tilted to provide access to tomographic equipment supported by the gantries.

The top plan view of FIG. 3 illustrates the components of a two-gantry frame in accordance with the principles of the present invention. In this illustrative embodiment, the PET scanner gantry 108, mounted on movable stand 110, has been separated from the CT scanner gantry 106 that is mounted on the fixed stand 114. In this view, the CT scanner gantry 106 is tilted to provide better access to components housed within the gantry 106. The base 102 is fully extended, as is the linear guide 104. The end elevation view of FIG. 4 illustrates the CT scanner gantry 106 tilted on the fixed stand 114, which supports it. The fixed stand is supported, in turn, by the base 102.

Although various exemplary embodiments of the invention have been disclosed, it will be apparent to those skilled in the art that various changes and modifications can be made which will achieve some of the advantages of the invention without departing from the spirit and scope of the invention. It will be evident to those reasonably skilled in the art that other components performing the same functions may be suitably substituted. The foregoing description of specific embodiments of the invention has been presented for the purposes of illustration and description. It is not intended to be exhaustive or to limit the invention to the precise forms disclosed, and many modifications and variations are possible in light of the above teachings. The embodiments were chosen and described to best explain the principles of the invention and its practical application, and to thereby enable others skilled in the art to best utilize the invention. It is intended that scope of the invention be limited only by the claims appended hereto.

What is claimed is:

1. A multi-scanner system comprising:
   a base;
   a linear guide supported by the base; and
   a plurality of scanner gantries, at least one gantry supported by the linear guide such that said gantry may be moved along the linear guide relative to at least one other gantry, and at least one of the gantries is pivotally mounted.

2. The multi-scanner system of claim 1, wherein the scanner gantries include at least one CT scanner gantry.

3. The multi-scanner system of claim 1, wherein the scanner gantries include at least one PET scanner gantry.

4. The multi-scanner system of claim 1, further including a scanner stand supported by the linear guide.

5. The multi-scanner system of claim 4, wherein the scanner stand is a CT scanner stand for supporting a CT gantry, said CT gantry including means for tilting the gantry supported by the CT scanner stand.

6. The multi-scanner system of claim 1, wherein the base includes a retractable extension.

7. The multi-scanner system of claim 1, wherein the linear guide includes a retractable extension.

8. A multi-scanner tomography system comprising:
   a base;
   a plurality of tomography scanners;
   a linear guide supported by the base; and
   a plurality of scanner gantry stands, wherein each stand respectively supports one of the tomography scanners and at least one stand is supported by the linear guide such that the tomography scanner supported by said at least one stand is movable along the linear guide relative to at least one other tomography scanner, and one of said scanners is tiltable.

9. The system of claim 8, wherein the plurality of tomography scanners include at least two modalities.

10. The system of claim 9, wherein the modalities include PET and CT scanning modalities.

11. The multi-scanner system of claim 8, wherein the scanner gantries include at least one CT scanner gantry.

12. The multi-scanner system of claim 8, wherein the scanner gantries include at least one PET scanner gantry.

13. The multi-scanner system of claim 8, wherein the scanner stand supported by the linear guide is a CT scanner stand.

14. The multi-scanner system of claim 13, wherein the CT scanner stand includes means for tilting the gantry supported by the CT scanner stand.

15. The multi-scanner system of claim 8, wherein the base includes a retractable extension.

16. The multi-scanner system of claim 8, wherein the linear guide includes a retractable extension.

17. The multi-scanner system of claim 8, further comprising one or more clamps configured to hold a movable gantry in a preferred position upon said linear guide upon activation of said one or more clamps.

18. The multi-scanner system of claim 17, wherein said clamps are friction clamps.

19. The multi-scanner system of claim 8, wherein the scanner stand supported by the linear guide is a PET scanner stand.

20. A multi-scanner tomography system comprising:

a base;

a plurality of tomography scanners;

a linear guide supported by a base; and a plurality of scanner gantry stands, at least one stand supported by the linear guide such that said stand may be moved along the linear guide relative to at least one other gantry, and at least one of the gantries is pivotally mounted, each stand supporting one of said tomography scanners;

wherein one of said base and linear guide include a retractable extension.

* * * * *